United States Patent
Xu et al.

(10) Patent No.: US 10,835,605 B2
(45) Date of Patent: Nov. 17, 2020

(54) PREPARATIONS OF POLY(LACTIC-CO-GLYCOLIC ACID)/POLYDOPAMINE CORE/SHELL HYBRID NANOPARTICLE FOR PHOTOTHERMAL APPLICATIONS

(71) Applicant: UNIVERSITY OF SOUTH CAROLINA, Columbia, SC (US)

(72) Inventors: Peisheng Xu, Chapin, SC (US); Huacheng He, Columbia, SC (US)

(73) Assignee: University of South Carolina, Columbia, SC (US)

( * ) Notice: Subject to any disclaimer, the term of this patent is extended or adjusted under 35 U.S.C. 154(b) by 18 days.

(21) Appl. No.: 15/269,058

(22) Filed: Sep. 19, 2016

(65) Prior Publication Data

US 2017/0095558 A1   Apr. 6, 2017

Related U.S. Application Data

(60) Provisional application No. 62/235,721, filed on Oct. 1, 2015.

(51) Int. Cl.
| | | |
|---|---|---|
| A61K 41/00 | (2020.01) | |
| A61K 31/704 | (2006.01) | |
| A61N 5/06 | (2006.01) | |
| A61K 9/00 | (2006.01) | |
| A61K 47/69 | (2017.01) | |
| A61K 9/51 | (2006.01) | |
| A61K 47/68 | (2017.01) | |

(52) U.S. Cl.
CPC ........ *A61K 41/0057* (2013.01); *A61K 9/0009* (2013.01); *A61K 9/513* (2013.01); *A61K 31/704* (2013.01); *A61K 41/0028* (2013.01); *A61K 41/0052* (2013.01); *A61K 47/6849* (2017.08); *A61K 47/6935* (2017.08); *A61K 47/6937* (2017.08); *A61N 5/062* (2013.01); *A61N 5/0625* (2013.01); *A61N 2005/0659* (2013.01)

(58) Field of Classification Search
None
See application file for complete search history.

(56) References Cited

U.S. PATENT DOCUMENTS

| 8,809,277 B2 | 8/2014 | Xu et al. |
|---|---|---|
| 9,168,230 B2 | 10/2015 | Xu et al. |
| 2016/0108160 A1 | 4/2016 | Xu et al. |
| 2016/0346208 A1 | 12/2016 | Xu et al. |

OTHER PUBLICATIONS

Park et al (Polydopamine-Based Simple and Versatile Surface Modification of Polymeric Nano Drug Carriers. ACS Nano, 2014, 8 (4), pp. 3347-3356).*

Gao et al (A Sweet Polydopamine Nanoplatform for Synergistic Combination of Targeted Chemo-Photothermal Therapy. A Sweet Polydopamine Nanoplatform for Synergistic Combination of Targeted Chemo-Photothermal Therapy. Macromol. Rapid Commun., 36: 916-922 (published online Apr. 1, 2015)).*

Xi et al (Au nanoparticle-coated, PLGA-based hybrid capsules for combined ultrasound imaging and HIFU therapy. Cite this: J. Mater. Chem. B, Apr. 16, 2015, 3, 4213-4220).*

Makadia et al (Poly Lactic-co-Glycolic Acid (PLGA) as Biodegradable Controlled Drug Delivery Carrier. Polymers (Basel). Sep. 1, 2011; 3(3): 1377-1397). Year: 2011).*

Khan, M. S.; Vishakante, G. D.; Siddaramaiah, H. Gold Nanoparticles: A Paradigm Shift in Biomedical Applications. Adv. Colloid Interface Sci. 2013, 199, 44-58.

Liu, X. S.; Huang, N.; Li, H.; Wang, H. B.; Jin, Q.; Ji, J. Multidentate Polyethylene Glycol Modified Gold Nanorods for in Vivo near-Infrared Photothermal Cancer Therapy. ACS Appl. Mater. Interfaces 2014, 6, 5657-5668.

Chen, J.; Wiley, B.; Li, Z. Y.; Campbell, D.; Saeki, F.; Cang, H.; Au, L.; Lee, J.; Li, X.; Xia, Y. Gold Nanocages: Engineering Their Structure for Biomedical Applications. Adv. Mater. 2005, 17, 2255-2261.

Wang, S. H.; Riedinger, A.; Li, H. B.; Fu, C. H.; Liu, H. Y.; Li, L. L.; Liu, T. L.; Tan, L. F.; Barthel, M. J.; Pugliese, G.; De Donato, F.; D'Abbusco, M. S.; Meng, X. W.; Manna, L.; Meng, H.; Pellegrino, T. Plasmonic Copper Sulfide Nanocrystals Exhibiting near-Infrared Photothermal and Photodynamic Therapeutic Effects. ACS Nano 2015, 9, 1788-1800.

Alkilany, A. M.; Thompson, L. B.; Boulos, S. P.; Sisco, P. N.; Murphy, C. J. Gold Nanorods: Their Potential for Photothermal Therapeutics and Drug Delivery, Tempered by the Complexity of Their Biological Interactions. Adv. Drug Delivery Rev. 2012, 64, 190-9.

Kwon, K. C.; Ryu, J. H.; Lee, J. H.; Lee, E. J.; Kwon, I. C.; Kim, K.; Lee, J. Proteinticle/Gold Core/Shell Nanoparticles for Targeted Cancer Therapy without Nanotoxicity. Adv. Mater. 2014, 26, 6436-41.

Zhang, Z.; Wang, J.; Chen, C. Near-Infrared Light-Mediated Nanoplatforms for Cancer Thermo-Chemotherapy and Optical Imaging. Adv. Mater. 2013, 25, 3869-80.

Skrabalak, S. E.: Chen, J.; Au, L.; Lu, X.; Li, X.; Xia, Y. Gold Nanocages for Biomedical Applications. Adv. Mater. 2007, 19, 3177-3184.

Dong, W.; Li, Y.; Niu, D.; Ma, Z.; Gu, J.; Chen, Y.; Zhao, W.; Liu, X.; Liu, C.; Shi, J. Facile Synthesis of Monodisperse Superparamagnetic Fe3o4 Core@Hybrid@Au Shell Nanocomposite for Bimodal Imaging and Photothermal Therapy. Adv. Mater. 2011, 23, 5392-7.

(Continued)

*Primary Examiner* — Jake M Vu
(74) *Attorney, Agent, or Firm* — Dority & Manning, P.A.

(57) ABSTRACT

Described is a biodegradable and biocompatible hybrid nanoparticle for use in photothermal applications. The hybrid nanoparticle includes a poly(lactide-co-glycolic acid) core and a polydopamine shell. Optionally, the hybrid nanoparticle can be loaded with an active agent such as an anti-cancer agent. The hybrid nanoparticles can include detection agents, targeting agents, etc. The nanoparticles can be useful for disease detection, treatment, and monitoring.

17 Claims, 7 Drawing Sheets

(56) References Cited

OTHER PUBLICATIONS

Yavuz, M. S.; Cheng, Y.; Chen, J.; Cobley, C. M.; Zhang, Q.; Rycenga, M.; Xie, J.; Kim, C.; Song, K. H.; Schwartz, A. G.; Wang, L. V.; Xia, Y. Gold Nanocages Covered by Smart Polymers for Controlled Release with near-Infrared Light. Nat. Mater. 2009, 8, 9:35-9.

Dickerson, E. B.; Dreaden, E. C.; Huang, X.; El-Sayed, I. H.; Chu, H.; Pushpanketh, S.; McDonald, J. F.; El-Saved, M. A. Gold Nanorod Assisted near-Infrared Plasmonic Photothermal Therapy (Pptt) of Squamous Cell Carcinoma in Mice. Cancer Lett. 2008, 269, 57-66.

Loo, C.; Lin, A.; Hirsch, L.; Lee, M. H.; Barton, J.; Halas, N.; West, J.; Drezek, R. Nanoshell-Enabled Photonics-Based Imaging and Therapy of Cancer. Technol. Cancer Res. Treat. 2004, 3, 33-40.

Khlebtsov, N.; Dykman, L. Biodistribution and Toxicity of Engineered Gold Nanoparticles: A Review of in Vitro and in Vivo Studies. Chem. Soc. Rev. 2011, 40, 1647-1671.

Fraga, S.; Brandao, A.; Soares, M. E.; Morais, T.; Duarte, J. A.; Pereira, L.; Soares, L.; Neves, C.; Pereira, E.; Bastos, M. D.; Carmo, H. Short- and Long-Term Distribution and Toxicity of Gold Nanoparticles in the Rat after a Single-Dose Intravenous Administration. Nanomedicine 2014, 10, 1757-1766.

Sun, B.; Ranganathan, B.; Feng, S. S. Multifunctional Poly(D,L-Lactide-Co-Glycolide)/Montmorillonite (Plga/Mmt) Nanoparticles Decorated by Trastuzumab for Targeted Chemotherapy of Breast Cancer. Biomaterials 2008, 29, 475-486.

Zhang, Z. P.; Lee, S. H.; Feng, S. S. Folate-Decorated Poly(Lactide-Co-Glycolide)-Vitamin E Tpgs Nanoparticles for Targeted Drug Delivery. Biomaterials 2007, 28, 1889-1899.

Fazio, E.; Scala, A.; Grimato, S.; Ridolfo, A.; Grassi, G.; Neri, F. Laser Light Triggered Smart Release of Silibinin from a Pegylated-Plga Gold Nanocomposite. J. Mater. Chem. B 2015, 3, 9023-9032.

Song, J. B.; Yang, X. Y.; Jacobson, O.; Huang, P.; Sun, X. L.; Lin, L. S.; Yan, X. F.; Niu, G.; Ma, Q. J.; Chen, X. Ultrasmall Gold Nanorod Vesicles with Enhanced Tumor Accumulation and Fast Excretion from the Body for Cancer Therapy. Adv. Mater. 2015, 27, 4910-4917.

Liu, Y. L.; Ai, K. L.; Lu, L. H. Polydopamine and Its Derivative Materials: Synthesis and Promising Applications in Energy, Environmental, and Biomedical Fields. Chem. Rev. 2014, 114, 5057-5115.

Lee, H.; Dellatore, S. M.; Miller, W. M.; Messersmith, P. B. Mussel-Inspired Surface Chemistry for Multifunctional Coatings. Science 2007, 318, 426-430.

Ye, Q.; Zhou, F.; Liu, W. M. Bioinspired Catecholic Chemistry for Surface Modification. Chem. Soc. Rev. 2011, 40, 4244-4258.

Liu, Y. L.; Ai, K. L.; Liu, J. H.; Deng, M.; He, Y. Y.; Lu, L. H. Dopamine-Melanin Colloidal Nanospheres: An Efficient near-Infrared Photothermal Therapeutic Agent for in Vivo Cancer Therapy. Adv. Mater. 2013, 25, 1353-1359.

Yang, Y.; Bajaj, N.; Xu, P.; Ohn. K.; Tsifansky, M. D.; Yeo, Y. Development of Highly Porous Large Plga Microparticles for Pulmonary Drug Delivery. Biomaterials 2009, 30, 1947-53.

Park, J.; Brust, T. F.; Lee, H. J.; Lee, S. C.; Watts, V. J.; Yeo, Y. Polydopamine-Based Simple and Versatile Surface Modification of Polymeric Nano Drug Carriers. ACS Nano 2014, 8, 3347-3356.

Yang, J.; Lee, J.; Kang, J.; Oh, S. J.; Ko, H. J.; Son, J. H.; Lee, K.; Suh, J. S.; Huh, Y. M.; Haam, S. Smart Drug-Loaded Polymer Gold Nanoshells for Systemic and Localized Therapy of Human Epithelial Cancer. Adv. Mater. 2009, 21, 4339-4342.

Wang, X. Y.; Zhang, J. S.; Wang, Y. T.; Wang, C. P.; Xiao, J. R.; Zhang, Q.; Cheng, Y. Y. Multi-Responsive Photothermal-Chemotherapy with Drug-Loaded Melanin-Like Nanoparticles for Synergetic Tumor Ablation. Biomaterials 2016, 81, 114-124.

Cheng, B.; He, H.; Huang, T.; Berr, S. S.; He, J.; Fan, D.; Zhang, J.; Xu, P. Gold Nanosphere Gated Mesoporous Silica Nanoparticle Responsive to near-Infrared Light and Redox Potential as a Theranostic Platform for Cancer Therapy. J. Biomed. Nanotechnol. 2016, 12, 435-449.

Lin, L.-S.; Yang, X.; Niu, G.; Song, J.; Yang, H.-H.; Chen, X. Dual-Enhanced Photothermal Conversion Properties of Reduced Graphene Oxide-Coated Gold Superparticles for Light-Triggered Acoustic and Thermal Theranostics. Nanoscale 2016, 8, 2116-2122.

Yewale, C.; Baradia, D.; Vhora, I.; Patil, S.; Misra, A. Epidermal Growth Factor Receptor Targeting in Cancer: A Review of Trends and Strategies. Biomaterials. 2013, 34, 8690-8707.

Song, X.; Gong, H.; Yin, S.; Cheng, L.; Wang, C.; Li, Z.; Li, Y.; Wang, X.; Liu, G.; Liu, Z. Ultra-Small Iron Oxide Doped Polypyrrole Nanoparticles for in Vivo Multimodal Imaging Guided Photothermal Therapy. Adv. Funct. Mater. 2014, 24, 1194-1201.

Li, Z.; Huang, H.; Tang, S.; Li, Y.; Yu, X.-F.; Wang, H.; Li, P.; Sun. Z.; Zhang, H.; Liu, C.; Chu, P. K. Small Gold Nanorods Laden Macrophages for Enhanced Tumor Coverage in Photothermal Therapy. Biomaterials. 2016, 74, 144-154.

Piao, J.-G.; Wang, L.; Gao, F.; You, Y.-Z.; Xiong, Y.; Yang, L. Erythrocyte Membrane Is an Alternative Coating to Polyethylene Glycol for Prolonging the Circulation Lifetime of Gold Nanocages for Photothermal Therapy. ACS Nano. 2014, 8, 10414-10425.

Bi, H.; Dai, Y.; Lv, R.; Zhong, C.; He, F.; Gai, S.; Gulzar, A.; Yang, G.; Yang, P. Doxorubicin-Conjugated Cus Nanoparticles for Efficient Synergistic Therapy Triggered by near-Infrared Light. Dalton Trans. 2016. 45, 5101-5110.

Chatterjee, K.; Zhang, J. Q.; Honbo, N.; Karliner, J. S. Doxorubicin Cardiomyopathy. Cardiology. 2010, 115, 155-162.

Miyata, M.; Suzuki, S.; Misaka, T.; Shishido, T.; Saitoh, S.I.; Ishigami, A.; Kubota, I.; Takeishi, Y. Senescence marker protein 30 has a cardio-protective role in doxorubicin-induced cardiac dysfunction. PLoS One, 2013, 8, e79093.

Al-Harthi, S. E.; Alarabi, O. M.; Ramadan, W. S.; Alaama, M. N.; Al-Kreathy, H. M.; Damanhouri, Z. A.; Khan, L. M.; Osman, A. M. M. Amelioration of Doxorubicin-Induced Cardiotoxicity by Resveratrol. Mol. Med. Rep. 2014, 10, 1455-1460.

Ma, H.; Jones, K, R.; Guo, R.; Xu, P.; Shen, Y.; Ren, J. Cisplatin Compromises Myocardial Contractile Function and Mitochondrial Ultrastructure: Role of Endoplasmic Reticulum Stress. Clin. Exp. Pharmacol. Physiol, 2010, 37, 460-465.

* cited by examiner

PREPARATIONS OF POLY(LACTIC-CO-GLYCOLIC ACID)/POLYDOPAMINE CORE/SHELL HYBRID NANOPARTICLE FOR PHOTOTHERMAL APPLICATIONS

CROSS REFERENCE TO RELATED APPLICATION

This application claims filing benefit of U.S. Provisional Patent Application Ser. No. 62/235,721 having a filing date of Oct. 1, 2015, which is incorporated herein by reference in its entirety.

BACKGROUND

Photothermal therapy (also called photothermal ablation); photothermal radiation and optical hyperthermia are therapies gaining interest for treatment and detection of disease. According to the methods, a photothermal substrate is located in the vicinity of a targeted cell mass or tissue and excited with electromagnetic radiation at a specific wavelength band. This activation brings the substrate to an excited state where it then releases energy in the form of heat. The local increase in temperature can destroy diseased cells in the vicinity.

Beneficially, photothermal therapy does not require oxygen to generate the temperature increase, which makes it very attractive for in vivo applications. Photothermal therapy has several additional advantages including relatively simple methodology, fast patient recovery, few side effects, low invasiveness, and little or no hospitalization. In addition, the process can utilize relatively long wavelength light, e.g., infrared (IR) or near-infrared (NIR), which is low energy and therefore less harmful to healthy cells and tissues through which the energy passes before interacting with the photothermal substrate. The use of light in the NIR spectrum has additional merits due to high spatial accuracy.

Several different types of nanostructures have been utilized as substrates in photothermal therapy methodology, including aggregated gold nanoparticles, gold nanoshells, gold nanocages, core-free Au/Ag dendrites, gold nanorods, carbon nanotubes, and graphite. Gold nanorods have gained special interest, since the light absorption range can be finely tuned by adjusting the aspect ratio. Gold nanorods have other advantages as well including efficient large scale synthesis, easy functionalization, high photothermal inversion and colloidal stability.

Despite their advantages, existing photothermal substrates present challenges, particularly for in vivo applications. For instance, gold nanorods are often prepared by a seed-mediated synthesis and include a bilayer capping of cetyltrimethylammonium bromide (CTAB) which shows cytotoxicity, thus limiting the clinical application. In addition, the unsatisfied payload-carrying capacity of known photothermal substrates has hindered their clinical translation. In addition, known materials are generally not biodegradable, and as such will either remain in the subject's body or, if expelled, need to be recovered in order to avoid release into the environment.

While the above describes improvement in the art, room for further improvement exists. For instance, biodegradable and biocompatible materials that can integrate both photothermal therapy and drug delivery modules into one system would be of great benefit.

SUMMARY

According to one embodiment, disclosed are methods for photothermal therapy utilizing hybrid core/shell nanoparticles as the photothermal substrate. The hybrid nanoparticles include a poly(lactide-co-glycolic acid) (PLGA) core and a polydopamine (PD) coating on the core. The hybrid nanoparticles are biocompatible and biodegradable, and can be beneficially utilized in photothermal therapy in a wide variety of applications. In one embodiment, the hybrid nanoparticles can be loaded with a bioactive agent and utilized as a drug delivery vehicle, for instance in conjunction with photothermal therapeutic uses.

A method can include irradiating the hybrid nanoparticles with near-infrared (NIR) light. For instance, in one embodiment a method can include locating a hybrid nanoparticle in an environment, the environment comprising a living cell, and directing NIR light at the hybrid nanoparticle (e.g., from about 640 nanometers to about 900 nanometers). The interaction between the hybrid nanoparticles and the NIR increases the temperature in the environment surrounding the hybrid nanoparticles, which can lead to cell destruction, optionally in conjunction with drug delivery.

BRIEF DESCRIPTION OF THE FIGURES

A full and enabling disclosure of the present invention, including the best mode thereof, directed to one of ordinary skill in the art, is set forth in the specification, which makes reference to the appended figures, in which.

Figure 1:
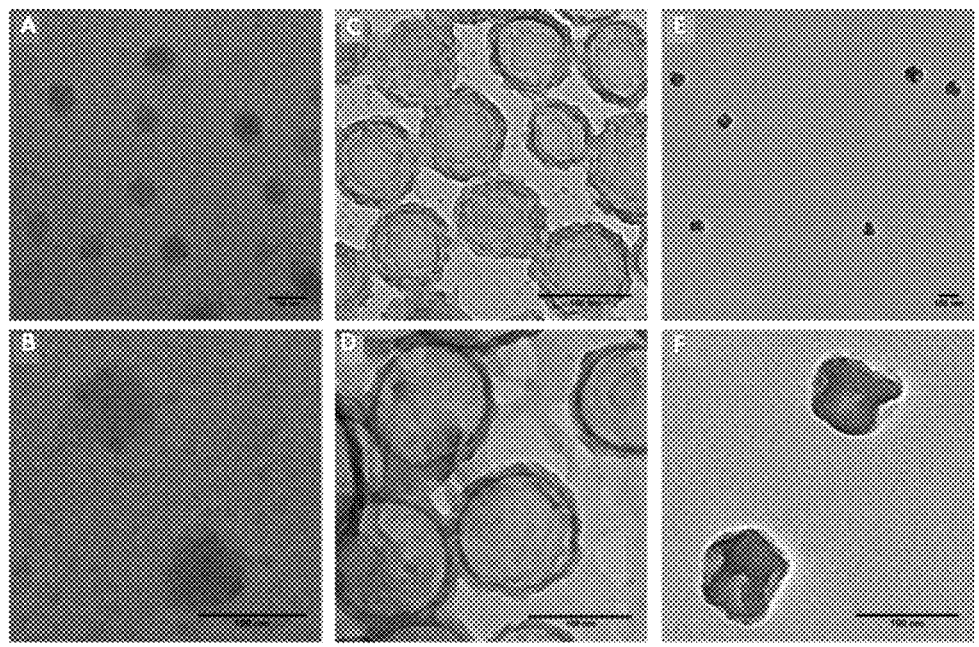
FIG. 1 presents transmission electron microscope (TEM) images of PLGA nanoparticles (Panel A and Panel B), PLGA/PD hybrid nanoparticles (Panel C and Panel D) and PLGA/PD hybrid nanoparticles following irradiation (Panel E and Panel F). The scale bars are 100 nm.

Repeat use of reference characters throughout the present specification and appended drawings is intended to represent same or analogous features or elements of the invention.

DETAILED DESCRIPTION

The following description and other modifications and variations to the presently disclosed subject matter may be practiced by those of ordinary skill in the art, without departing from the spirit and scope of the present disclosure. In addition, it should be understood that aspects of various embodiments may be interchanged both in whole and in part. Furthermore, those of ordinary skill in the art will appreciate that the following description is by way of example only, and is not intended to limit the disclosed subject matter.

The present disclosure is generally directed to a hybrid nanoparticle-based therapeutic/diagnostic platform that can be utilized for disease detection, drug delivery, photothermal therapy, and other biomedical applications. More specifically, disclosed are hybrid nanoparticles that include a poly(lactic-co-glycolic acid) (PLGA) core and a polydopamine (PDA) shell. Beneficially, the disclosed nanoparticles are biocompatible and can be formed form well characterized materials that are completely biodegradable and FDA approved for safety. The nanoparticles can be effectively utilized for drug delivery in conjunction with photothermal therapeutic applications under near-infrared (NIR) irradiation, and release of the payloads from the nanoparticles can be remotely controlled by the photothermal irradiation. The hybrid nanoparticles can be beneficially utilized in a wide variety of biomedical applications including, but not limited to, drug delivery, gene delivery, cancer therapy, atherosclerosis treatment, pet sterilization, and disease diagnostics.

According to the present disclosure, the core/shell hybrid nanoparticles can be formed by conjugating polydopamine onto the surface of nanoparticles formed of poly(lactide-co-glycolic acid). The hybrid nanoparticles can display excellent photothermal converting ability as well as high drug loading capacity and triggerable drug release. For instance, hybrid nanoparticles loaded with a chemotherapy agent such as doxorubicin (DOX) can be sensitive to both NIR irradiation and intracellularly elevated redox potential. Thus, chemotherapy loaded hybrid nanoparticles coupled with NIR irradiation can exhibit a synergistic effect of both photothermal therapy and chemotherapy in killing cancer cells.

The hybrid nanoparticles can also be utilized in detection. For instance, the hybrid nanoparticles can be labeled with a detectable substance, e.g., $^{64}Cu$. The labeled hybrid nanoparticles can be used to successfully detect the existence of clinically relevant targets, e.g., tumors through PET imaging.

The PLGA copolymer of the core can be any biodegradable polyester polymer selected from the groups comprising lactic acid and glycolic acid monomer units. For instance, the PLGA copolymer can encompass, without limitation, poly(D-lactide-co-glycolic acid), poly(L-lactide-co-glycolic acid), poly(D,L-lactide-co-glycolic acid), and derivatives thereof. In addition, the copolymer can include additional biocompatible, biodegradable monomer residues including, for example, caprolactone monomers, hydroxyalkanoate monomers, and so forth. The PLGA copolymers can be random copolymer or block copolymers, as desired.

The PLGA copolymer of the core can encompass a wide range of molecular weights and ratios of lactic acid residues to glycolic acid residues. For example, the biodegradable polyester copolymer can have a number average molecular weight of from about 1,000 Da to about 300,000 Da, from about 10,000 Da to about 200,000 Da, or from about 15,000 Da to about 100,000 Da in some embodiments. The molar ratio of lactide to glycolide in the copolymer be in the range of from about 1:10 to 10:1 in some embodiments, for instance from about 80:20 to about 20:80, from about 40:60 to about 60:40, or about 50:50 in some embodiments.

Various commercially available PLGA copolymers may be used. For example, poly (D,L-lactide-co-glycolic acid) is commercially available from Medisorb® Technologies International L.P. (Cincinnati, Ohio). A suitable product commercially available from Medisorb is a 50:50 poly (D,L-lactide-co-glycolic acid) known as Medisorb®50:50 DL. This product has a mole percent composition of 50% lactide and 50% glycolide, Other suitable commercially available products are Medisorb® 65:35 DL, 75:25 DL, and 85:15 DL. Poly(lactide-co-glycolide) is also commercially available from Boehringer Ingelheim (Germany) under its Resomer mark. e.g., PLGA 50:50 (Resomer® RG 502), PLGA 75:25 (Resomer® RG 752) and d,1-PLA (Resomer® RG 206), and from Birmingham Polymers (Birmingham, Ala.).

While the hybrid nanoparticles can be utilized in one embodiment for only the photothermal affect, in some embodiments, the core nanoparticles can contain an active agent for delivery in conjunction with the photothermal process. The amount of such agent incorporated in the hybrid nanoparticles can for example range from about 1 wt. % to about 90 wt. %, about 30 to 50 wt. %, or about 35 to 40 wt. % of the weight of the core nanoparticle in some embodiments.

Illustrative examples of molecules that can be incorporated in the core of the hybrid nanoparticle include biologically active compounds such as peptides, proteins, therapeutic agents, and diagnostic agents as well as combinations of two or more different agents. Incorporated agents may comprise but are not limited to anticancer agents such as dideoxyinosine, floxuridine, 6-mercaptopurine, doxorubicin, daunorubicin, L-darubicin, cisplatin, mitoxantrone, 5-fluorouracil, epirubicin, adriamycin, taxol, etc.; antibiotics such as erythromycin, vancomycin, oleandomycin, ampicillin, etc.; anticoagulant such as heparin; germicides such as ara-A, acrylguanosine, nordeoxyguanosine, azidothymidine, dideoxyadenosine, dideoxythymidine, etc.; protein therapeutics such as insulin, calcitonin, ACTH, glucagon, somatostatin, somatotropin, somatomedin, parathyroid hormone, erythropoietin, hypo-thalmic releasing factors, prolactin, thyroid stimulating hormone, endorphins, enkephalins, vasopressin, non-naturally occurring opioids, superoxide dismutase, interferon, asparaginase, arginase, arginine deaminease, adenosine deaminase ribonuclease, trypsin, chemotrypsin, and pepsinantiarrythmic agent; prodrugs and derivatives thereof.

The method used to incorporate an active agent in the core of the hybrid particle should consider drug property, nanoparticle quality, scale-up feasibility, manufacturing costs, personnel safety, environmental impact, waste disposal, and the like. There are many different techniques used to prepare PLGA Nano particulate carriers, all of which are encompassed herein. Representative examples are single or double emulsion solvent evaporation/extraction, salting-out (coacervation), hot melt microencapsulation (congealing), spray drying, nanoprecipitation, membrane emulsification, microfluidic technology, supercritical fluid methods, and flow focusing. These encapsulation methods share a common feature of mixing a PLGA dispersed organic phase (in the form of either bulk or droplets) with antisolvent. Solvent removal is usually performed by evaporation, extraction, and/or combination of both.

Solvent evaporation and solvent extraction methods utilize volatile organic solvents for dissolving the PLGA. Commonly used organic solvents are methylene chloride, ethyl acetate, and methyl ethyl ketone. A double emulsion process as is known in the art can be used for producing PLGA particles containing water-soluble drugs, including protein drugs. Both solid/oil/water (s/o/w) and water/oil/water (w/o/w) systems are used depending on the type of active agent. Generally, the active agent in soluble or dispersed form is added to the polymer solution, and the mixture is then emulsified in an aqueous phase containing a surface-active agent, such as poly(vinyl alcohol). In the solvent evaporation method, the organic solvent is evaporated by raising the temperature and/or by applying vacuum. In the solvent extraction method, the organic solvent diffuses into the water phase to make emulsion droplets into solid polymer microspheres. In both methods, the continuous phase can be non-miscible oils. The organic solvent conventionally employed in this method is a chlorinated hydrocarbon, such as methylene chloride, of which a residual amount can be strictly controlled for the known toxicities.

The coacervation method is based on salting out (or phase separation) from a homogeneous polymer solution of hydrophilic polymers into small droplets of a polymer-rich, second liquid phase, rather than into solid aggregates. When an aqueous polymer solution is partially dehydrated (or desolvated) by adding a strongly hydrophilic substance (e.g., sodium sulfate) or a water-miscible, non-solvent (e.g., ethanol, acetone, dioxane, isopropanol, or propanol), the water-soluble polymer is concentrated in water to form the polymer-rich phase. This is known as "simple" coacervation. If water-insoluble drug particles are present as a suspension or as an emulsion, the polymer-rich phase is formed on the drug particle surface to form a capsule under suitable conditions. In "complex" coacervation, the polymer-rich complex (coacervate) phase is induced by interaction between two dispersed hydrophilic polymers (colloids) of opposite electric charges. Since electrostatic interactions are involved, the pH of the medium is important to control the charges of the polymers as is known.

In hot melt microencapsulation (also called congealing) a solid drug or liquid drug is mixed with the polymer melted at high temperatures. The mixture is then suspended in a non-miscible solvent with continuous stirring at a temperature several degrees above the melting point of the polymer. After the emulsion is stabilized, the system is cooled until the polymer particles solidify. In this process, the drug has to be stable at the polymer melting temperature. For interfacial cross-linking, the polymer can possess functional groups that can be cross-linked by ions or multi-functional molecules Interfacial polymerization requires monomers that can be polymerized at the interface of two immiscible substances to form a membrane, and thus removal of the unreacted monomers from the final product can become an issue.

For spray drying, a drug is dissolved or suspended in a suitable (either aqueous or non-aqueous) solvent that contains dissolved polymer materials. The drug can be dissolved or suspended in the solvent. Alternatively, the drug solution can be emulsified in the polymer solution. The solution is atomized and microspheres are dried by a heated carrier gas. The particle size can be controlled by the rate of spraying, the feed rate of the drug-polymer solution, the nozzle size, and temperature in the drying and cooling chambers.

Particles that incorporate an active agent can be prepared by rapid expansion of supercritical solutions (RESS) and supercritical antisolvent crystallization (SAS). RESS exploits the liquid-like solvent power of the supercritical fluids whereas SAS uses supercritical fluid as an antisolvent. Carbon dioxide is most commonly used for the critical conditions are easily attainable, i.e., $T_c=31°$ C. and $P_c=73.8$ bar. It is also environmentally benign, relatively non-toxic, non-inflammable, inexpensive, and has a reasonably high dissolving power.

The average size, distribution, and shape of the particles can be controlled as is known, for instance by varying the concentration of the reactants and particle formation conditions. In some embodiments, the PLGA nanoparticles may be substantially spherical. However, the PLGA nanoparticles can have shapes other than substantially spherical shapes. The term nanoparticles as used herein is intended the include particles as large as about 1000 nm in average diameter. In general, the PLGA nanoparticles can have an average diameter of about 10 nanometers or greater, for instance about 20 nanometers or greater, for instance from about 10 nanometers to about 500 nanometers in largest cross sectional dimension, or from about 20 to about 300 nanometers in largest cross sectional dimension in some embodiments, as measured by transmission electron microscopy (TEM) or similar visualization technique. Particle size does not refer to agglomerates in solution or suspension.

The nanoparticles include a shell of polydopamine surrounding the PLGA core. The polydopamine shell can be formed via polymerization of dissolved dopamine on the core or via bonding of the pre-formed polymer to the nanoparticle core. Beneficially, the PLGA nanoparticle core can include suitable reactive functionality to provide bonding sites for the dopamine-based shell material.

The polydopamine shell can be formed in one embodiment via polymerization of a dopamine monomer onto the surface of the previously formed PLGA shell. For example, a method can include formation of a dispersion of the PLGA core nanoparticles, optionally incorporating one or more active agents. Following, the nanoparticles held in the dispersion can be contacted with a buffered solution having a pH greater than 7 and comprising a dopamine compound of the following general structure:

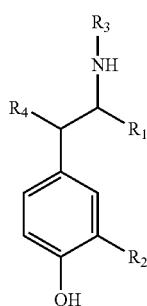

in which
R$_1$ represents a hydrogen atom or —COOH,
R$_2$ represents a hydrogen atom or —OH,
R$_3$ is hydrogen or C1-C6 group and
R$_4$ represents a hydrogen atom hydrogen or —OH.

Upon contact, the polydopamine can polymerize via condensation to the surface of the PLGA nanoparticle core.

According to one embodiment, in the dopamine compound above, at least one of R$_1$, R$_3$ and R$_4$ is hydrogen. In some embodiments, the group R$_2$ is OH. In one embodiment, the dopamine compound can be selected from dopamine, L-dopa, epinephrine and norepinephrine. For instance, dopamine of the following formula can be polymerized to form the shell of the hybrid nanoparticles:

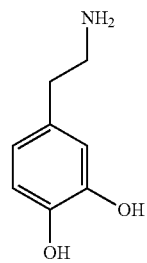 [SMILES: NCCc1ccc(O)c(O)c1]

According to one such embodiment, the polydopamine of the shell can have the following general structure:

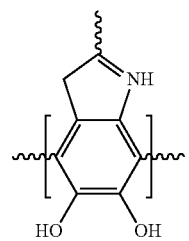

Optionally, the hybrid nanoparticle can include additional materials. Additional materials can be a component of the PLGA core, the PD shell, both the core and the shell, and/or a component of a secondary shell formed either internal or external to the PD core of the hybrid nanoparticles.

By way of example, other agents as may be incorporated within or on the nanoparticles either alone or in conjunction with another active agent can include photosensitizers. A photosensitizer can meet one or all of the following conditions: (1) maximum absorption wavelength between 600-800 nm, and limited absorption between 400-600 nm; (2) high singlet oxygen yield; (3) strong phototoxicity and weak dark toxicity; (4) high retention ratio in malignant tumor tissues; (5) single component; and (6) fluorescence. A photosensitizer as can be incorporated in a hybrid nanoparticle can include, without limitation, haematoporphyrins, phthalocyanine, chlorophylls, porphin or their derivatives such as acidified porphyrin, hemoporphyrin and their derivatives thereof, or the metal ion-complex of phthalocyanine and derivatives thereof, and so forth.

Other polymers may be formed in conjunction with the polydopamine or following formation of the polydopamine shell. For instance, polyethylene glycol (PEG) can be formed on the core/shell nanoparticle to modify characteristics of the hybrid nanoparticles.

Targeting ligands can be incorporated on the hybrid nanoparticles in some embodiments. For example, the hybrid system can be capable of detecting clinically relevant spontaneous tumors by use of a targeting ligand following which the hybrid nanoparticles can provide the synergetic effect of photothermal therapy and chemotherapy in killing the detected cancer cells. By way of example, tumor targeting ligands, such as RGD peptide, folic acid, and anisamide, which target cancer cells overexpressed integrins, folate, and sigma-2 receptors, respectively, can be ligated to the hybrid nanoparticles.

The hybrid nanoparticle can be delivered to a site, e.g., an in vivo site by use of the targeting ligands or any other directed delivery methodology. Following delivery, the hybrid nanoparticles can be subjected to IR or near IR radiation, e.g., radiation of from about 650 nanometers to about 900 nanometers in wavelength to trigger the photothermal effect of the nanoparticles. The release of a bioactive agent from the hybrid nanoparticles can be triggered by intracellular elevated redox potential as well as by the irradiation, which can improve control of drug delivery by use of the hybrid nanoparticles.

The present disclosure may be better understood with reference to the Examples set forth below.

EXAMPLE 1

Fabrication of PLGA and Doxorubicin Loaded PLGA Nanoparticle (DOX@PLGA)

Doxorubicin (DOX) loaded poly(lactic-co-glycolic acid) nanoparticles (DOX@PLGA) were fabricated by emulsion method. Briefly, 5 mg DOX was first dissolved in 1 mL CH$_3$OH with 25 μL triethylamine (TEA) and added into 5 mL CH$_2$Cl$_2$ with 200 mg PLGA (50/50, 16 kDa). The solution was then combined with 20 mL 5% polyvinyl alcohol (PVA, Mw=9000-10000 Da) solution on ice, followed by ultrasonication for 15 min at 400 W. After sonication, the resulting emulsion was added into 100 mL H$_2$O and stirred overnight to evaporate the organic solvent.

Following formation, the DOX@PLGA nanoparticles were centrifuged at 1000 rcf. for 10 min to remove aggregates and then centrifuged at 16000 rcf. for 15 min to collect the particles. The particles were washed by ddH$_2$O three times to remove excess PVA and non-encapsulated DOX.

Empty PLGA nanoparticles were fabricated following the method described above except DOX was not introduced during the preparation of the emulsion mixture. The resulting nanoparticle palette was redispersed in 10 mL H$_2$O and kept at 4° C. for further use.

Polydopamine Coating

A dopamine shell was formed on the PLGA nanoparticles and on the DOX@PLGA nanoparticles. Briefly, 6 mg of the PLGA or DOX@PLGA nanoparticles were dispersed in 12 mL tris buffer (10 mM, pH 8.5) including 6 mg dissolved dopamine. The mixture was kept stirring for 3 h at room temperature in an opened glass vial. The solution turned to light brown first and eventually to dark brown, indicating the successful coating of polydopamine on the nanoparticles. Finally, the hybrid nanoparticles were collected by centrifuging at 16,000 rcf. for 10 min, washed for three times with ddH$_2$O, and redispersed in 6 mL tris buffer (20 mM, pH 8.5) for PEG decoration.

PEG Decoration

DOX@PLGA/PD nanoparticles (2 mL) prepared above was combined with 4 mg PEG-SH (Mw: 2000 Da) in 2 mL PBS buffer and sonicated for 30 min. Then the pH of mixture solution was immediately adjusted to 7.0. The PEG decorated nanoparticles were collected by centrifuging at 16,000 rcf. for 10 min at 4° C., washed twice with PBS, and redispersed in 500 µL PBS 7.4 (10 mM) and stored in 4° C.

Nanoparticle Characterization

TEM images showing the morphology of PLGA nanoparticles (FIG. 1, Panel A and Panel B) and DOX@PLGA/PD nanoparticles prior to NIR irradiation (FIG. 1, Panel C and Panel D) and following irradiation (FIG. 1, Panel E and Panel F) were obtained and the hydrodynamic size and zeta potential of nanoparticles were measured by Zeta sizer Nano-ZS.

The DOX concentration was measured by fluorescence (Ex=485 nm, Em=595 nm) by dissolving nanoparticles in DMSO and calculated according the calibration curve of DOX.

Figure 2:
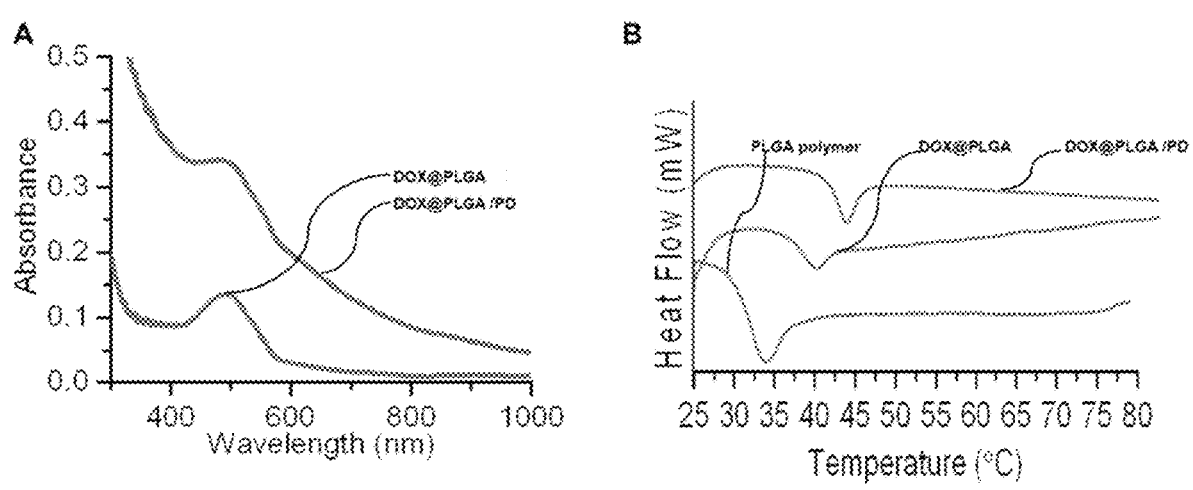
FIG. 2 presents the UV-vis spectrum (A) and differential scanning calorimetry (DSC) curves (B) of PLGA nanoparticles, PLGA nanoparticles loaded with doxorubicin (DOX@PLGA), and PLGA/PD core/shell nanoparticles loaded with doxorubicin (DOX@PLGA/PD).

The UV-Vis spectrum before and after dopamine coating of DOX@PLGA nanoparticle was recorded at the DOX concentration equal to 10 µg/mL (FIG. 2 at A).

To quantify drug loading efficiency and loading content, nanoparticles were freeze dried. For DLS, nanoparticles were dispersed in 1 mM PBS 7.4 (0.2 mg/mL). The glass transition temperature of the nanoparticles was measured by Differential Scanning Calorimetry (Q2000, TA Instruments, heated from −15° C. to 180° C. with a heat flow rate of 10° C./min) results for the PLGA polymer, DOX@PLGA nanoparticle and DOX@PLGA/PD nanoparticle are shown in FIG. 2 at B.

Photothermal Conversion Efficiency Calculation

Figure 3:
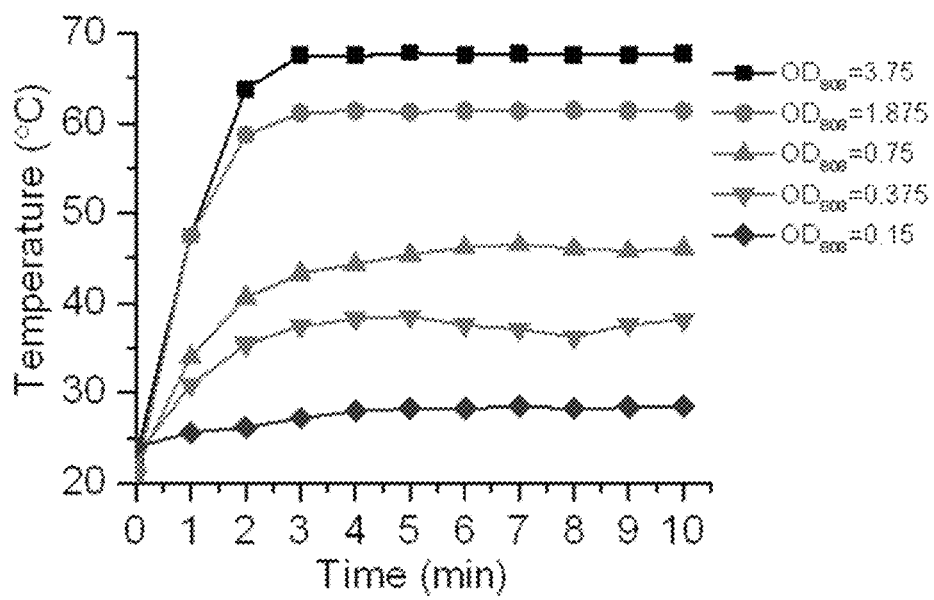
FIG. 3 graphically illustrates the photothermal effect of polydopamine coated PLGA nanoparticle. A nano-suspension of polydopamine coated PLGA nanoparticles was irradiated by a 808 nm laser (2.83 W/cm$^2$).

To test the photothermal effect of PLGA/PD nanoparticles, 50 µL nanoparticles in PBS 7.4 (10 mM) were irradiated with a 808 nm NIR laser (2.83 W/cm$^2$, Scorpius-D IR Portable Laser, Laserglow Technologies) for 10 min. The temperature of the nanoparticles were measured every 1 min by FLIR thermal camera (FLIR i7, FLIR® Systems, Inc.). Results are shown in FIG. 3

In Vitro DOX Release

Figure 4:
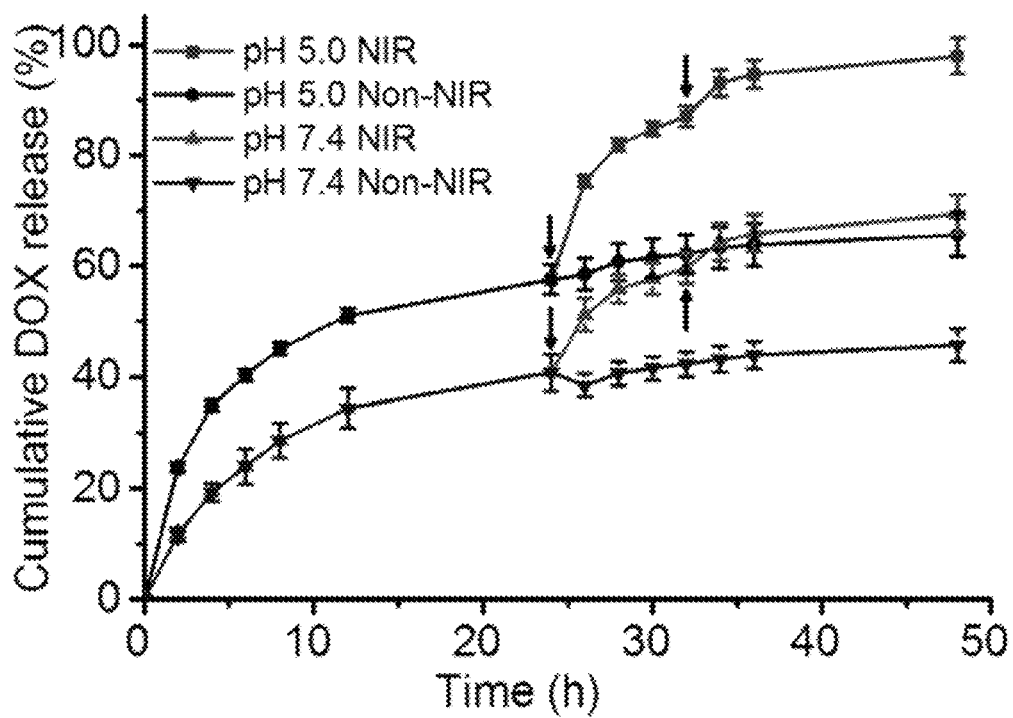
FIG. 4 illustrates the release kinetics of doxorubicin from DOX@PLGA/PD. The black arrows indicate the time points when the irradiation (10 min, 2.83 W/cm$^2$) was applied. Data were presented as mean±SD, n=3.

The release profile of the DOX from the nanoparticles was measured at pH 5.0 and pH 7.4 with and without laser irradiation. Briefly, DOX@PLGA/PD-PEG nanoparticles were dispersed in 500 µL acetate buffer (10 mM, pH 5.0) and PBS buffer (10 mM, pH 7.4) respectively and incubated at 37° C. Both buffers were supplemented with 2% Tween 80 to improve the solubility of DOX. The DOX concentration was equal to 20 µg/mL. Each pH group included six parallel samples. At pre-determined time points, all samples were centrifuged at 16,000 g for 10 min. 250 µL supernatants were retrieved and refilled with 250 µL fresh buffer to redisperse the nanoparticles. At 24 h and 32 h post incubation, three samples in each pH group were irradiated under 808 nm laser for 10 min while the other three samples were kept at 37° C. All samples were continuously incubated up to 72 h. Following, the releasing of DOX from the nanoparticles was quantified by a microplate reader ((Ex=495 nm, Em=595 nm, Beckman Coulter DTX 880 Multimode Detector, Beckman Coulter, Inc.). Results are illustrated in FIG. 4.

Live & Dead Cell Assay

Figure 5:
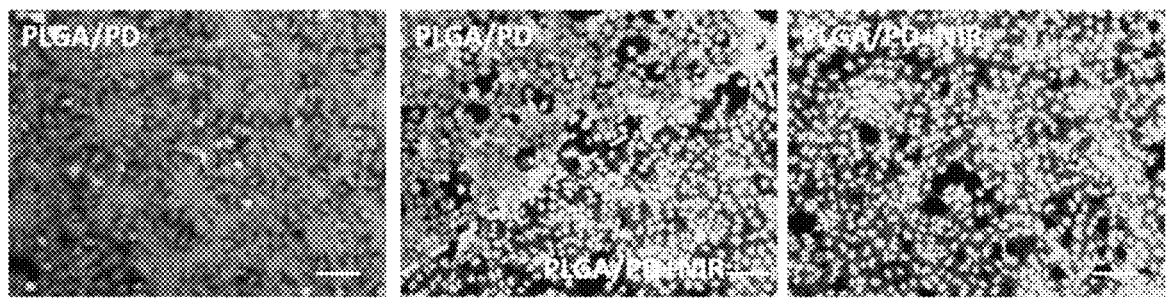
FIG. 5 illustrates the fluorescent images of live/dead cell assay after NIR irradiation. Cells were treated with PLGA/PD (left), PLGA/PD and half NIR irradiation (center), and PLGA/PD and NIR irradiation (right), respectively. The laser dose was 30 min, 2.83 W/cm$^2$. Scale bars are 100 μm.

To study the photothermal cytotoxicity of the nanoparticles, Live and Dead cell assays were carried out. Briefly, UMSCC 22A cells (300,000cells/well) were seeded in a 6-well plate and incubated under a humidified atmosphere of 95/5% air/CO$_2$ until 100% confluence. After 24 h of incubation, PLGA/PD nanoparticles were added to the plate. The equivalent DOX concentration was 10 µg/mL and the PLGA weight amounts were kept the same in all nanoparticles. Cells were incubated at 37° C. for another 2 h, and exposed to the 808 nm NIR laser for 30 min. Following, cells were very gently washed by PBS (2×). Calcein AM (0.2 µM) and propidium iodide (PI, 25 µg/mL) mixture solution (500 µL) was then added and the resulting solution held at room temperature for 30 min. The cells were observed directly by fluorescence microscopy (Olympus IX81, Olympus America Inc.). Results are illustrated in FIG. 5, in which the left panel illustrates the non-irradiated cells, the central panel illustrates non-irradiated cells in the upper left half and irradiated cells in the lower right have, and irradiated cells are shown in the right panel.

In Vitro Cytotoxicity

Figure 6:
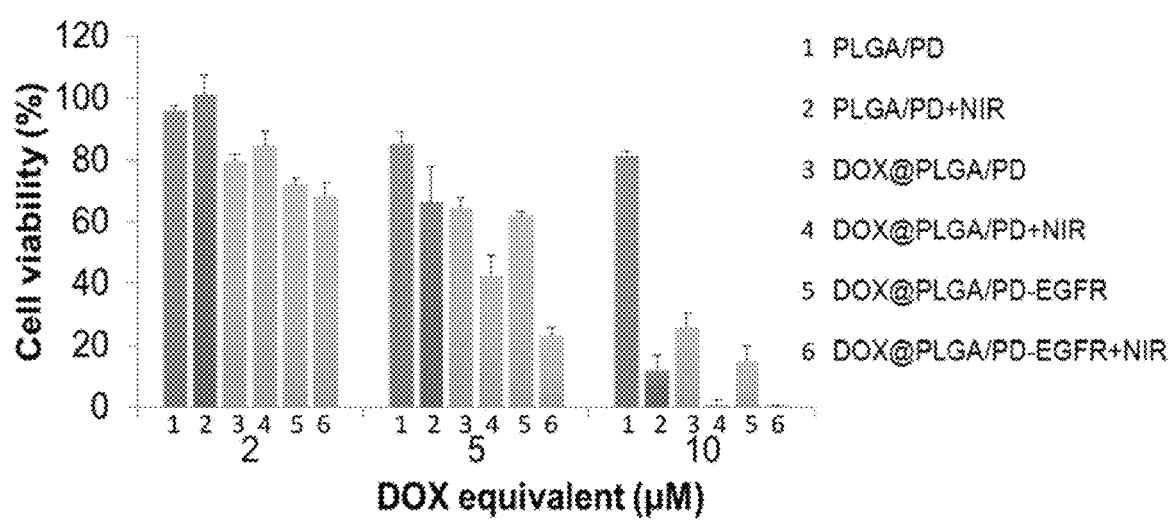
FIG. 6 graphically illustrates cell viability of UMSCC 22A cells after being treated with DOX@PLGA/PD and NIR irradiation. Cells were co-incubated with nanoparticles for 3 h prior to the NIR irradiation with a 808 nm laser for 10 min (2.83 W/cm$^2$). Data were presented as mean±SD, n=3.

The cytotoxicity of nanoparticles was evaluated by MTT assay. UMSCC 22A cells were seeded in 96-well plate (20,000 cells/well) for 24 h prior to the study. Following, either free DOX or DOX@PLGA/PD-PEG nanoparticles with DOX concentration equal to 2, 5 and 10 µg/mL were added. For comparison, PLGA/PD-PEG (no DOX encapsulation) nanoparticles were also added. The cells were then incubated 3 h in 95/5% air/CO$_2$ at 37° C. followed by irradiation under a 808 nm laser for 10 min. After that, all wells were washed 2 times and replaced with fresh culture medium and kept incubation for another 24 h. Finally, MTT reagent (100 µL, 10%(w/w) in medium) was added and incubated for 4h, following the addition of MTT stop solution and the measurement of the optical density of the medium using a microplate reader (ELX808, Bio-Tech Instrument, Inc.) at λ=595 nm. Results are shown in FIG. 6.

EXAMPLE 2

DOX encapsulated PLGA nanoparticles were fabricated by emulsion method as described above. The coating of dopamine on the DOX@PLGA nanoparticle was formed as described above.

Testing Protocols

Unless noted otherwise, nanoparticle characterization and nanoparticle decoration methodologies were carried out as described above in Example 1. Nanoparticles were decorated with either PEG (DOX@PLGA/PD-PEG) or an antiepidural growth factor receptor (EGFR) antibody (Cetuximab) (DOX@PLGA/PD-C) as a targeting agent. EGFR is overexpressed in many types of cancer, including colon cancer, lung cancer, glioblastoma multiforme, and head and neck cancer, and thus was selected as a widely applicable targeting agent for examination. It was found that the Cetuximab conjugation efficiency was 59.6%.

Serum Stability

To investigate the serum stability, DOX@PLGA, DOX@PLGA/PD-PEG, and DOX@PLGA/PD-C were diluted with 10% FCS (equivalent DOX concentration was 15 µg/mL) and incubated at 37° C. for 7 days. The sizes of the nanoparticles were monitored by DLS to evaluate their stability in serum containing buffer.

Flow Cytometry

UMSCC 22A cells (300,000cells/well) were seeded in 6-well plates overnight. After that, DOX, DOX@PLGA/PD-PEG, and DOX@PLGA/PD-C nanoparticles were added at the DOX equivalent concentration of 1 µg/m L. In order to investigate the effect of EGFR on the cellular uptake of DOX@PLGA/PD-C nanoparticle, cells were pretreated with free anti-EGFR antibody (200 µg/mL) 30 min before adding DOX@PLGA/PD-C nanoparticles. The plate was incubated at 37° C. for 3 h. Then cells were washed, trypsinized and resuspended in PBS. DOX-positive cell population was quantified at Ex=488 nm, Em=585 nm using flow cytometry (BD Accuri C6, BD Biosciences).

Tumor Growth Inhibitory Assay

UMSCC 22A cells ($3 \times 10^6$ cells in 100 µL DMEM medium) were inoculated subcutaneously in female Balb/c nude mice (8-10 week old, ~20 g, Jackson Laboratory). The tumor volume was measured by a digital caliper and calculated according to the following formula: Tumor volume=tumor length)×(tumor width)$^2$/2. When the tumor reached to 50 mm$^3$, either free DOX or DOX@PLGA/PD-C were intratumorally injected (40 µL, DOX concentration equivalent to 15 µg/mL). For the control group, PBS was injected. Mice were exposed to an 808 nm laser irradiation (2.83 W/cm$^2$) 3 h post injection for 10 min. The temperature of the mice during the irradiation was recorded by the FLIR thermal camera. The tumor volumes (V) of the mice were measured every other day for 24 days. The relative tumor volume expressed as V/V$_0$ (V$_0$ was the tumor volume when the treatment was initiated) was used to represent the tumor size change during the whole treatment process. After 24 days, the mice were sacrificed and the blood, tumor, liver, heart, lung, kidneys, and spleen were collected for further analysis. All organs were firstly fixed in 10% neutral buffered formalin for 48 h and then washed with PBS and finally kept in 70% ethanol at 4° C.

Blood Analysis

Whole blood samples (50 µL) of the mice were firstly collected in heparinized tubes and analyzed with VetScan HM5 (Abaxis, Inc.) for white blood cells, red blood cells, neutrophils, etc.

TEM Analysis for Heart Tissue

To study the cardiotoxicity of DOX, the hearts of the mice were analyzed by TEM. The formalin fixed samples were further fixed with 1% perosmic oxide for 2 h at 4° C., washed with water and then dehydrated in a series of alcohol solutions, embedded, and sliced with the thickness between 50 and 70 nm. TEM analysis was performed on Hitachi H8000 operating at 200 kV.

Figure 7:
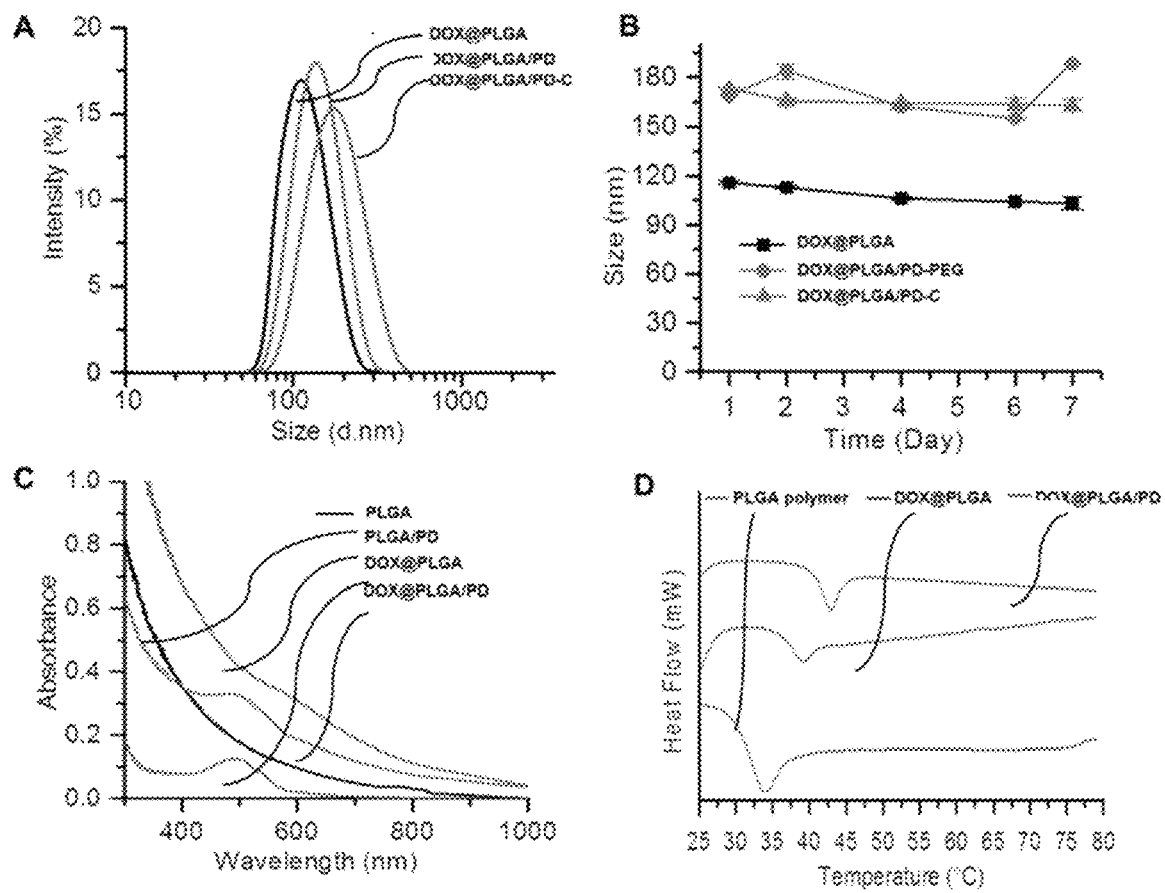
FIG. 7 presents physical properties of nanoparticles fabricated based on a PLGA polymer including the hydrodynamic size distributions of the different particles (Panel A), the serum stability of the different particles (Panel B), the UV-Vis spectra of the different particles (Panel C), and the glass transition temperatures of the different particles measured by differential scanning calorimetry (Panel D).

Dynamic light scattering (DLS) found that the size of DOX@PLGA was about 110 nm (FIG. 7, Panel A). The coating of PD layer increased the size of DOX@PLGA/PD to 135 nm. The addition of PEG protection layer and Cetuximab slightly increased the size of DOX@PLGA/PD-C nanoparticles, which coincided with the observation of TEM (FIG. 7, Panel A). To evaluate the nanoparticle stability during blood circulation, the size of the nanoparticles in 10% serum containing medium was monitored with DLS. Due to the existence of a PEG protection layer, DOX@PLGA/PD-C was stable in culture medium containing 10% FCS (FIG. 7, Panel B), and no obvious size change and aggregation were observed after one week of incubation. The absorbance of the nanoparticles shifted to the longer wavelength end after the coating of polydopamine (FIG. 7, Panel C). Differential scanning calorimetry (DSC) revealed that PD coating significantly increased the glass transition temperatures (T$_g$) of PLGA nanoparticle from 39.42 to 42.97° C. (FIG. 7, Panel D), suggesting that PLGA/PD nanoparticle could be a temperature sensitive carrier for targeted drug delivery.

Figure 8:
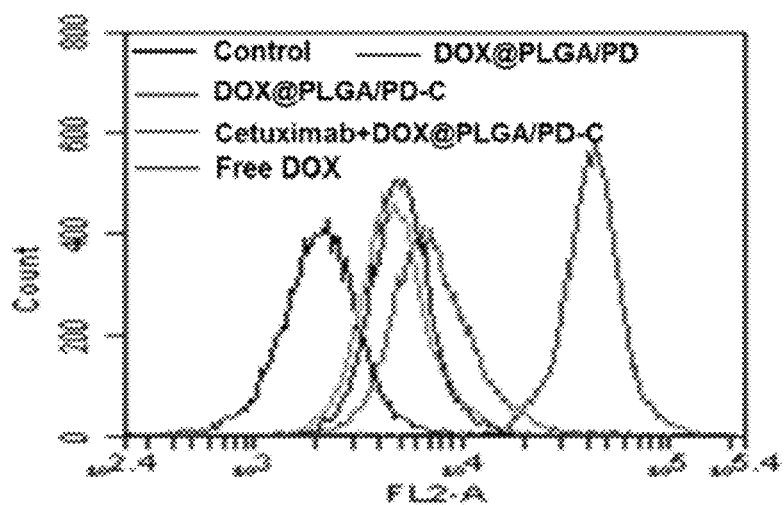
FIG. 8 presents flow cytometry spectra of UMSCC 22A cells treated with different conditions.

Confocal microscopy found that more red fluorescence signals were observed in cells treated with Cetuximab conjugated DOX@PLGA/PD-C than its non-targeted counterpart. In addition, the block of free Cetuximab significantly decreased the uptake of DOX@PLGA/PD-C nanoparticles, which EGFR mediated endocytosis. The EGFR mediated cellular uptake of DOX@PLGA/PD-C nanoparticles and blocking the effect of free Cetuximab were also observed by flow cytometry (FIG. 8). It was noted that free DOX entered cancer cells faster than the DOX@PLGA/PD-C nanoparticles (FIG. 8).

Figure 9:
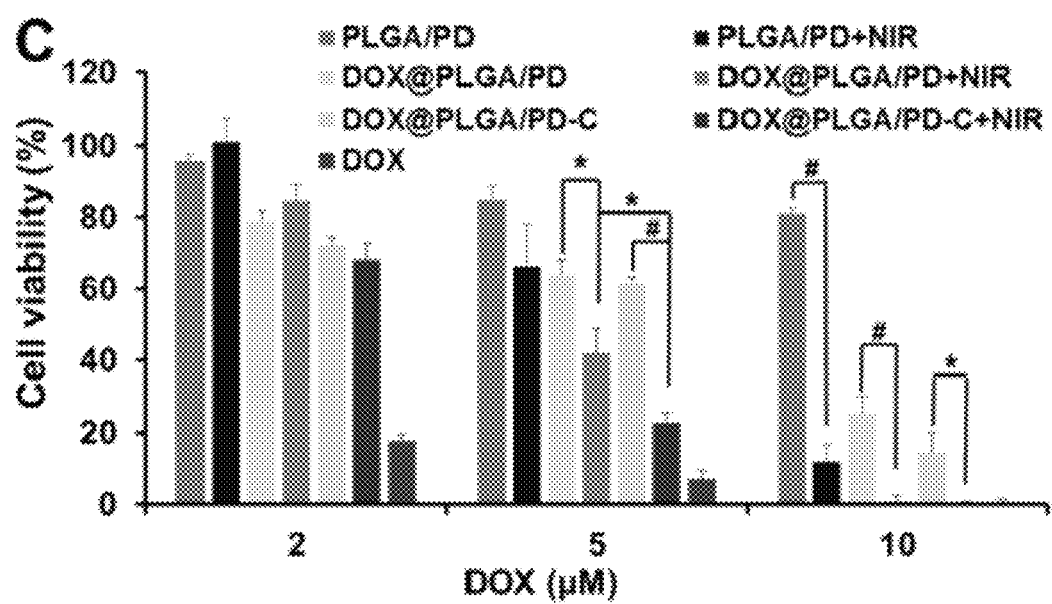
FIG. 9 presents cytotoxicity data of UMSCC 22A cells treated with different conditions. Cells received NIR irradiation for 10 min, 2.83 W/cm². MTT assay was carried out 24 h after the treatments. All scale bars equal to 50 μm.

To investigate whether the EGFR enhanced cellular uptake of DOX@PLGA/PD-C nanoparticles and if the photothermal effect of the nanoparticles can be translated into higher efficacy in killing cancer cells, cell proliferation assay was employed. As shown in FIG. 9, empty PLGA/PD nanoparticles were almost non-toxic, while effectively killing cancer cells when coupled with NIR irradiation. It is worth noting that the effect of NIR irradiation only became significant when PLGA/PD at the DOX corresponding of 5 µM or higher, at which PLGA/PD could generate enough heat to ablate cancer cells and augment drug release. The EGFR targeted nanoparticles showed much higher efficacy in killing UMSCC 22A cells than their non-targeted counterparts. As expected, NIR irradiation significantly boosted the potency of DOX@PLGA/PD and DOX@PLGA/PD-C, which reflects the combination effect of photothermal effect and its subsequent induced quicker drug release. Free DOX exhibited higher cell killing effect than other treatments except at 10 µM dose.

Figure 10:
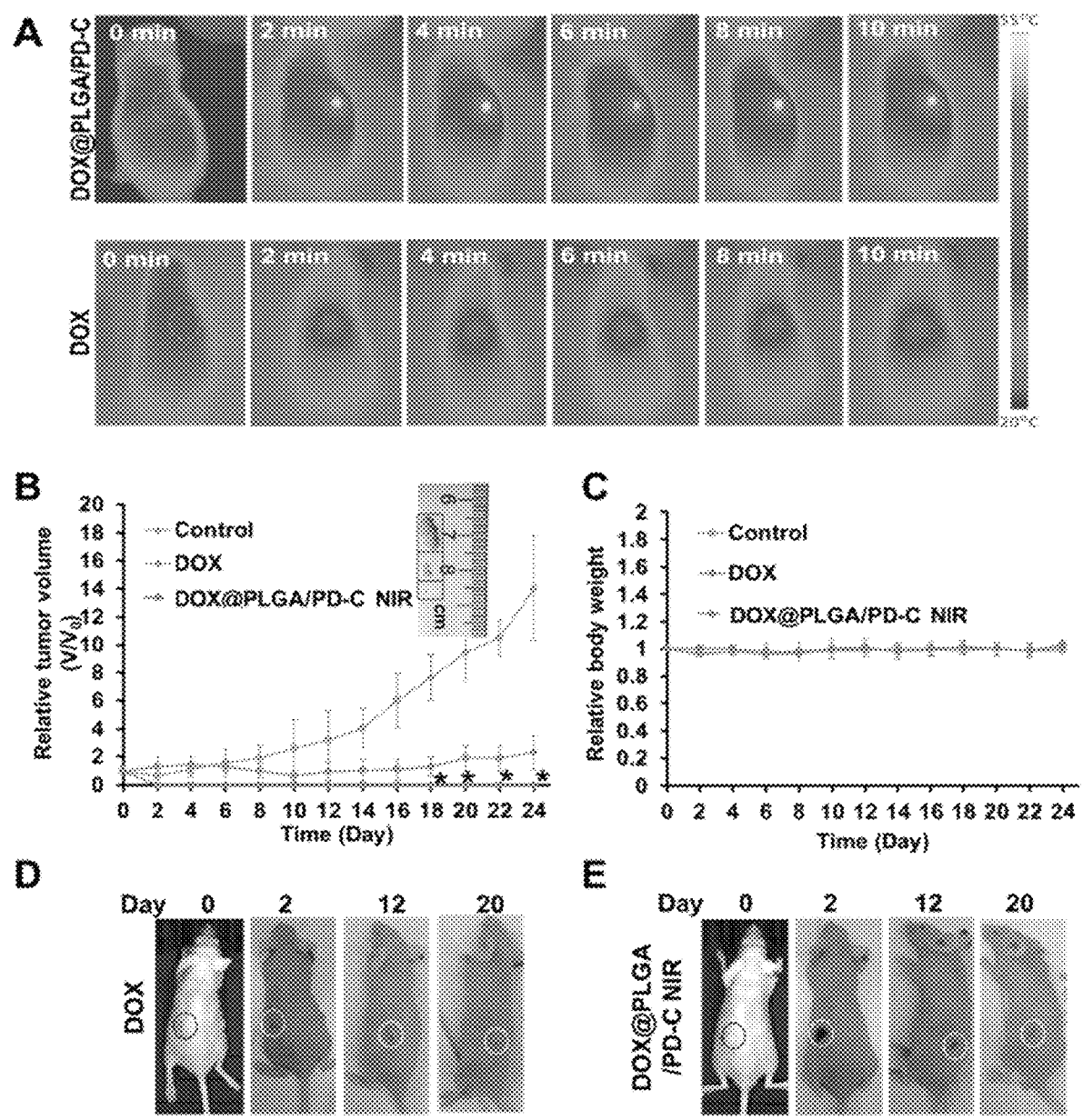
FIG. 10 illustrates in vivo tumor response after receiving different treatments. Panel A illustrates thermal images of mice after receiving NIR irradiation over 10 min (2.83 W/cm²) following administration of either free DOX or DOX-loaded nanoparticles that included a tumor targeting agent. Panel B presents the tumor volume change profiles of mice after receiving different treatments; the insert shows the representative images of tumors harvested from different treatment groups at the end of the experiment. Data were expressed as mean±SD (DOX@PLGA/PD-C NIR vs DOX, *P<0.05). Panel C presents the body weight curves of tumor-bearing mice after receiving different treatments. Panel D provides representative images of developed tumors after receiving DOX treatment. Panel E provides representative images of developed tumors after receiving DOX@PLGA/PD-C NIR treatment. Circles in Panels D and E indicate the location of the tumor.

To investigate the tumor growth inhibitory effect of EGFR targeted DOX@PLGA/PD coupled with NIR irradiation, a subcutaneous head and neck cancer mouse model was introduced. To maximize the therapeutic effect of the treatment, free DOX and EGFR targeted DOX@PLGA/PD nanoparticles were administrated intratumorally. The thermal images shown in FIG. 10 at Panel A indicated that EGFR targeted PLGA/PD could quickly elevate the temperature of tumor tissue to 55° C. within 2 min. For most developed photothermal systems, the temperature of treated tissues continuously increases when NIR irradiation is turned on. Interestingly, the PLGA/PD system treated tissue maintained its temperature constantly at 55° C. during the whole course of NIR irradiation. The tumor mass in the DOX@PLGA/PD-C coupled with NIR irradiation treatment group collapsed and formed a scar 2 days post treatment (FIG. 10, Panel E). The scar gradually disappeared and the original tumor did not recur during a 24-day period (FIG. 10, Panels B and E). Contrary to its strong potency shown in the in vitro study, free DOX treatment initially only slightly reduced tumor size (FIG. 10, Panels B and D). Furthermore, those tumors gradually bounced back 10 days post treatment. As expected, the non-treated tumors grew to 14 times of its initial size at the end of the experiment (FIG. 10, Panel B). No significant body weight change was observed in all groups (FIG. 10, Panel C). The negligible tumor mass in Panels B and E proved that DOX@PLGA/PD-C coupled with NIR irradiation was an effective approach for eradicating head and neck tumor.

Figure 11:
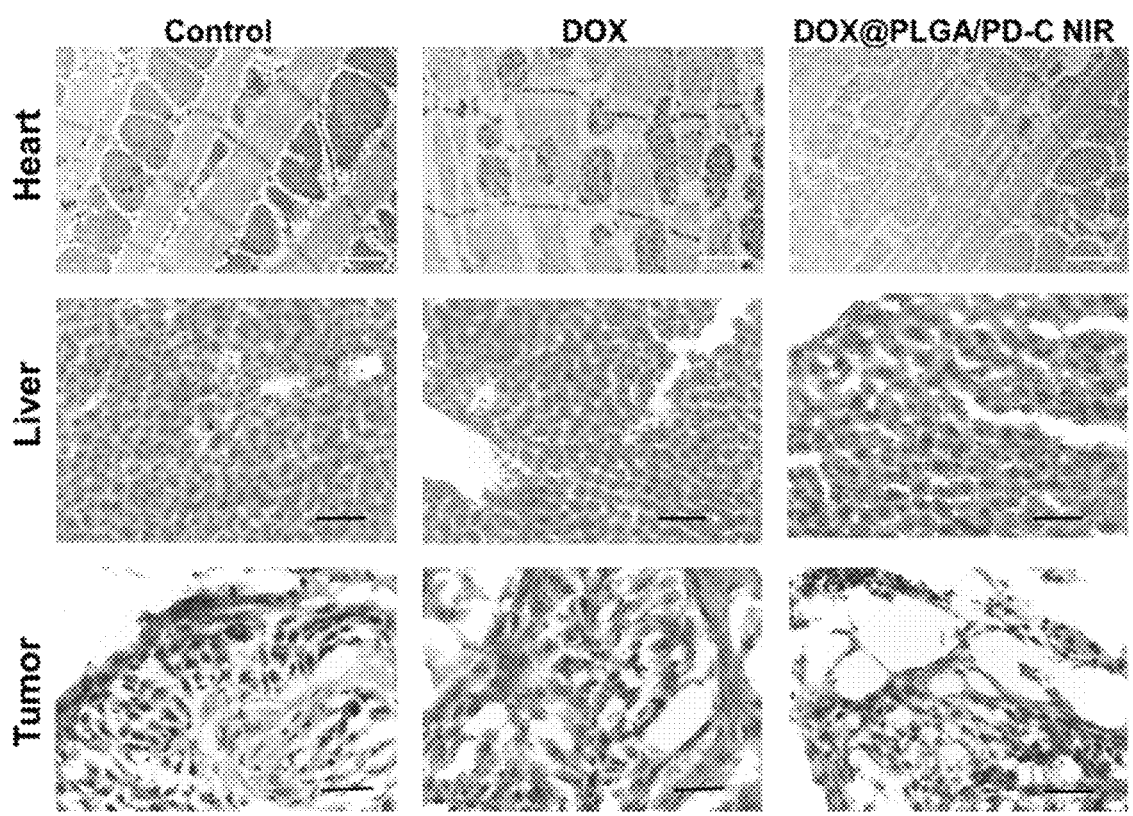
FIG. 11 presents TEM images of heart tissue sections and H&E staining images of liver and tumor tissue sections as described in the Examples section. Scale bars in the TEM images (top panel) and H&E staining sections (middle and bottom panels) are 1 μm and 50 μm, respectively.

To evaluate the safety of DOX@PLGA/PD-C coupled with NIR irradiation, hearts in the treated groups were collected and processed for TEM observation. TEM image (top panels of FIG. 11) revealed that the membrane integrity and ordered structure of mitochondria in the heart tissue from the mice receiving free DOX treatment have been significantly compromised. Surprisingly, no obvious structure abnormalcy was observed in the heart tissue in the DOX@PLGA/PD-C coupled with NIR irradiation treatment group. Furthermore, no histopathological changes were observed in the liver tissues among all treatment groups. Similarly, blood components analysis did not detect significant alteration among all treatment groups (data not shown). In addition, H&E staining of the tumor tissue (bottom panels of FIG. 11) showed that the control and DOX-treated tumors kept the characteristics of squamous cell carcinoma, while the apoptosis-related shrunk nuclei in the DOX@PLGA/PD-C coupled with NIR irradiation treated tumor proved its effectiveness. All these results indicate that DOX@PLGA/PD-C coupled with NIR irradiation is a safe tool.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A method for photothermal treatment compromising:
   irradiating a plurality of hybrid nanoparticles with near-infrared radiation for a time period, the hybrid nanoparticles each comprising a core and a shell, the core comprising poly(lactide-co-glycolic acid) and the shell comprising a polymer including residues of the following structure

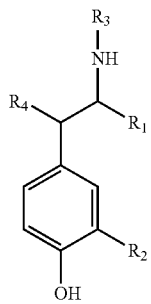

in which
   $R_1$ represents a hydrogen atom or —COOH,
   $R_2$ represents a hydrogen atom or —OH,
   $R_3$ represents a hydrogen atom or a C1-C6 group and
   $R_4$ represents a hydrogen atom or —OH,
   wherein, upon the irradiation, a temperature in a local environment surrounding the hybrid nanoparticles will increase for a first portion of the time period and will then stabilize following the first portion of the time period; and wherein upon irradiating the plurality of hybrid nanoparticles with near-infrared radiation for 10 minutes, a temperature profile of the local environment surrounding the hybrid nanoparticles will follow a temperature profile as in FIG. 3.

2. The method of claim 1, the core of the hybrid nanoparticles further comprising an active agent, the method further comprising releasing the active agent from the hybrid nanoparticles.

3. The method of claim 2, wherein the active agent is an anticancer agent, an antibiotic, an anticoagulant, a germicide, a protein therapeutic, a prodrug, or combinations of two or more active agents.

4. The method of claim 2, wherein the active agent is an anticancer agent.

5. The method of claim 1, the hybrid nanoparticles further comprising a photosensitizer.

6. The method of claim 1, the hybrid nanoparticles further comprising a detectable substance bonded to the hybrid nanoparticles, the method further comprising detecting the hybrid nanoparticles in the environment via the detectable substance.

7. The method of claim 1, the hybrid nanoparticles further comprising a targeting ligand bonded to the hybrid nanoparticles, the method further comprising adhering the hybrid nanoparticles to a target via the targeting ligand.

8. The method of claim 1, the poly(lactide-co-glycolic acid) having a number average molecular weight of from about 1,000 Daltons to about 300,000 Daltons.

9. The method of claim 1, wherein the residues comprise the following structure:

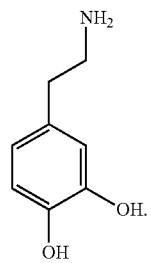 [SMILES: NCCc1ccc(O)c(O)c1]

10. The method of claim 1, wherein the electromagnetic radiation comprises near-infrared radiation at a wavelength of from about 640 nanometers to about 900 nanometers.

11. A method for photothermally treating a living cell comprising:
    locating a hybrid nanoparticle in an environment, the environment comprising a living cell, the hybrid nanoparticle comprising a core and a shell, the core comprising poly(lactide-co-glycolic acid) and the shell comprising a polymer including residues of the following structure;

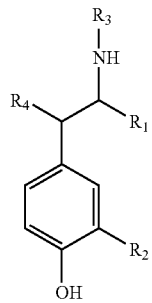

in which
    $R_1$ represents a hydrogen atom or —COOH,
    $R_2$ represents a hydrogen atom or —OH,
    $R_3$ is hydrogen or C1-C6 group and
    $R_4$ represents a hydrogen atom hydrogen or —OH; and Irradiating the hybrid nanoparticle in the environment with near-infrared light for a time period, the near-infrared light comprising a wavelength of from about 640 nanometers to about 900 nanometers, the interaction between the near-infrared radiation and the hybrid nanoparticle increasing the temperature in the environment for a first portion of the time period, and the temperature in the environment stabilizing following the first portion of the time period, and wherein upon irradiating the hybrid nanoparticles with the near-infrared radiation for 10 minutes, a temperature profile of the environment will follow a temperature profile as in FIG. 3.

12. The method of claim 11, further comprising releasing an active agent from the hybrid nanoparticle in the environment.

13. The method of claim 12, wherein the rate of release of the active agent from the hybrid nanoparticle is controlled by the near-infrared irradiation.

14. The method of claim 11, the hybrid nanoparticle further comprising a targeting ligand, the method further comprising binding the hybrid nanoparticle to the living cell via the targeting ligand.

15. The method of claim 11, the hybrid nanoparticle further comprising a detectable agent, the method further comprising detecting the hybrid nanoparticle in the environment via the detectable agent.

16. The method of claim 11, wherein the residues comprise the following structure:

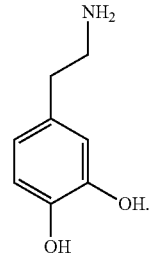 [SMILES: NCCc1ccc(O)c(O)c1]

17. The method of claim 1, wherein the first portion of the time period is 3 minutes.

* * * * *